(12) United States Patent
Ishikake et al.

(10) Patent No.: US 11,907,849 B2
(45) Date of Patent: Feb. 20, 2024

(54) INFORMATION PROCESSING SYSTEM, ENDOSCOPE SYSTEM, INFORMATION STORAGE MEDIUM, AND INFORMATION PROCESSING METHOD

(71) Applicants: OLYMPUS CORPORATION, Hachioji (JP); National University Corporation OITA UNIVERSITY, Oita (JP); Fukuoka Institute of Technology, Fukuoka (JP)

(72) Inventors: Makoto Ishikake, Hachioji (JP); Toshiya Kamiyama, Hachioji (JP); Masafumi Inomata, Oita (JP); Tsuyoshi Etoh, Oita (JP); Yukio Iwashita, Oita (JP); Makoto Nakashima, Oita (JP); Tatsushi Tokuyasu, Fukuoka (JP); Yusuke Matsunobu, Fukuoka (JP)

(73) Assignees: OLYMPUS CORPORATION, Hachioji (JP); National University Corporation OITA UNIVERSITY, Oita (JP); FUKUOKA INSTITUTE OF TECHNOLOGY, Fukuoka (JP)

( * ) Notice: Subject to any disclaimer, the term of this patent is extended or adjusted under 35 U.S.C. 154(b) by 497 days.

(21) Appl. No.: 17/333,935

(22) Filed: May 28, 2021

(65) Prior Publication Data
US 2021/0287395 A1 Sep. 16, 2021

Related U.S. Application Data

(63) Continuation of application No. PCT/JP2018/044121, filed on Nov. 30, 2018.

(51) Int. Cl.
*G06N 3/084* (2023.01)
*G06T 7/50* (2017.01)
(Continued)

(52) U.S. Cl.
CPC .......... *G06N 3/084* (2013.01); *G06F 18/214* (2023.01); *G06N 3/04* (2013.01); *G06T 7/0012* (2013.01);
(Continued)

(58) Field of Classification Search
CPC . G06N 3/084; G06N 3/04; G06T 7/50; G06T 7/73; G06T 7/0012; G06T 2207/20081;
(Continued)

(56) References Cited

U.S. PATENT DOCUMENTS

| 10,182,704 B2 | 1/2019 | Popovic |
| 2011/0245660 A1 | 10/2011 | Miyamoto |

(Continued)

FOREIGN PATENT DOCUMENTS

| EP | 3 603 479 A1 | 2/2020 |
| JP | 6-274634 A | 9/1994 |

(Continued)

OTHER PUBLICATIONS

International Search Report dated Feb. 19, 2019, issued in counterpart International Application No. PCT/JP2018/044121, with English Translation. (4 pages).

(Continued)

*Primary Examiner* — William D Titcomb
(74) *Attorney, Agent, or Firm* — WHDA, LLP

(57) ABSTRACT

An information processing system includes a storage device that stores therein a trained model, and a processor. The trained model is trained to output a position and shape of an object in a training image based on training data. The training data is data in which the training image is provided with an annotation indicating the position and shape of the object. The training image is an image captured with an angle of view including the object whose position and shape are not clearly displayed in an image. The processor (Continued)

BEFORE ANNOTATION

AFTER ANNOTATION executes detection processing on a detection image to output detected information indicating the position and shape of the object. The processor then causes a display device to display the detected information superimposed on the detection image.

16 Claims, 10 Drawing Sheets

(51) Int. Cl.
    *G06T 7/73*     (2017.01)
    *G06N 3/04*     (2023.01)
    *G06T 7/00*     (2017.01)
    *G06F 18/214*     (2023.01)
    *G06V 10/764*     (2022.01)

(52) U.S. Cl.
    CPC .................. *G06T 7/50* (2017.01); *G06T 7/73* (2017.01); *G06V 10/764* (2022.01); *G06T 2207/20081* (2013.01); *G06T 2207/20084* (2013.01); *G06T 2207/30024* (2013.01)

(58) Field of Classification Search
    CPC ........... G06T 2207/20084; G06T 2207/30024; G06V 10/764; G06F 18/214
    USPC .......................................................... 382/128
    See application file for complete search history.

(56) References Cited

U.S. PATENT DOCUMENTS

| | | | |
|---|---|---|---|
| 2012/0062714 A1 | 3/2012 | Liu et al. | |
| 2015/0254826 A1* | 9/2015 | Kanda | G06V 10/431 |
| | | | 382/128 |
| 2015/0356369 A1* | 12/2015 | Kitamura | G06T 7/0012 |
| | | | 382/128 |
| 2017/0004625 A1* | 1/2017 | Kamiyama | G06T 7/0016 |
| 2017/0309024 A1* | 10/2017 | Kitamura | G06T 7/11 |
| 2018/0014902 A1* | 1/2018 | Kitamura | A61B 1/045 |
| 2018/0070798 A1* | 3/2018 | Kamiyama | G06T 7/75 |
| 2018/0150675 A1* | 5/2018 | Kamiyama | A61B 5/00 |
| 2018/0184997 A1 | 7/2018 | Tsukagoshi et al. | |
| 2018/0322371 A1 | 11/2018 | Dupont De Dinechin et al. | |
| 2019/0022857 A1 | 1/2019 | Conus et al. | |
| 2019/0117167 A1* | 4/2019 | Kamiyama | A61B 1/04 |
| 2019/0244101 A1 | 8/2019 | Ando | |
| 2020/0146529 A1* | 5/2020 | Kono | G06T 7/0012 |
| 2021/0112197 A1* | 4/2021 | Shiraki | G06T 1/00 |
| 2021/0272284 A1* | 9/2021 | Kamiyama | G16H 50/70 |
| 2021/0287395 A1* | 9/2021 | Ishikake | G06V 10/764 |

FOREIGN PATENT DOCUMENTS

| | | |
|---|---|---|
| JP | 2011-212301 A | 10/2011 |
| JP | 2012-525898 A | 10/2012 |
| JP | 2017-177297 A | 10/2017 |
| JP | 2018-61771 A | 4/2018 |
| JP | 2018-200685 A | 12/2018 |
| WO | 2010/128411 A1 | 11/2010 |
| WO | 2017/195797 A1 | 11/2017 |
| WO | 2018/105138 A1 | 6/2018 |
| WO | 2018/180573 A1 | 10/2018 |

OTHER PUBLICATIONS

"Journal of Japan Society for Endoscopic Surgery", Programs of the 31st Annual Meeting of the Japan Society for Endoscopic Surgery, (2018), vol. 23, No. 7, With English Translation. (9 pages).

* cited by examiner

BEFORE ANNOTATION

AFTER ANNOTATION

INFORMATION PROCESSING SYSTEM, ENDOSCOPE SYSTEM, INFORMATION STORAGE MEDIUM, AND INFORMATION PROCESSING METHOD

CROSS REFERENCE TO RELATED APPLICATION

This application is a continuation of International Patent Application No. PCT/JP2018/044121, having an international filing date of Nov. 30, 2018, which designated the United States, the entirety of which is incorporated herein by reference.

BACKGROUND

A method of executing processing of detecting a recognition target from an image using machine learning has been known. For example, Japanese Unexamined Patent Application Publication No. 2018-61771 discloses a method of detecting a lesion from a medical image using machine learning. According to Japanese Unexamined Patent Application Publication No. 2018-61771, training data includes a plurality of regional images of a suspected lesion and an image feature label indicating a type of the lesion, and machine learning is performed based on the training data. The image feature label is used for identifying a magnitude of an area, a gray level, a tube shape, a bone contact type, or the like.

SUMMARY

According to an aspect of the present disclosure, an information processing system includes a storage device that stores therein a trained model, and a processor that executes detection processing based on the trained model. The trained model is trained to output the position and shape of the object in the training image based on training data, the training data being provided with an annotation indicating the position and shape of the object, the annotation being attached to the training image captured with an angle of view including an object whose position and shape are not clearly displayed in an image. The processor executes the detection processing on a detection image captured with an angle of view including the object, to output detected information indicating the position and shape of the object, and causing a display device to display the detected information superimposed on the detection image.

According to another aspect of the present disclosure, an endoscope system includes a processor unit including the information processing system described above, an endoscopic scope connected to the processor unit, and capturing the detection image and transmitting the detection image to the processor unit, and the display device connected to the processor unit, and displaying the detection image on which the detected information indicating the position and shape of the object is superimposed.

According to still another aspect of the present disclosure, an information storage medium stores therein a trained model. The trained model is used for causing a computer to function to execute detection processing of accepting an input of a detection image to a neural network and detecting an object, and cause a display device to display detected information indicating a position and shape of the object in the detection image superimposed on the detection image. The neural network includes an input layer taking input data, an intermediate layer executing computation processing on the data input through the input layer, and an output layer outputting data based on a computed result output from the intermediate layer. The trained model is trained to output the position and shape of the object in the training image based on training data, the training data being provided with an annotation indicating the position and shape of the object, the annotation being attached to the training image captured with an angle of view including an object whose position and shape are not clearly displayed in an image.

According to still another aspect of the present disclosure, an information processing method includes executing detection processing based on a trained model. The trained model is trained to output the position and shape of the object in the training image based on training data, the training data being provided with an annotation indicating the position and shape of the object, the annotation being attached to the training image captured with an angle of view including an object whose position and shape are not clearly displayed in an image. The method includes executing the detection processing based on the trained model on a detection image captured with an angle of view including the object, to output detected information indicating the position and shape of the object, and causing a display device to display the detected information superimposed on the detection image.

DESCRIPTION OF EXEMPLARY EMBODIMENTS

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

While a description will be hereinafter given of an example of cholecystectomy through laparoscopy, a target of application of the present embodiment is not limited to the cholecystectomy through laparoscopy. That is, the present embodiment is applicable in a case where machine learning is performed based on training data in which an image is provided with an annotation by an operator, and an object is detected from the image using a trained model.

1. Information Processing System and Endoscope System

Figure 1:
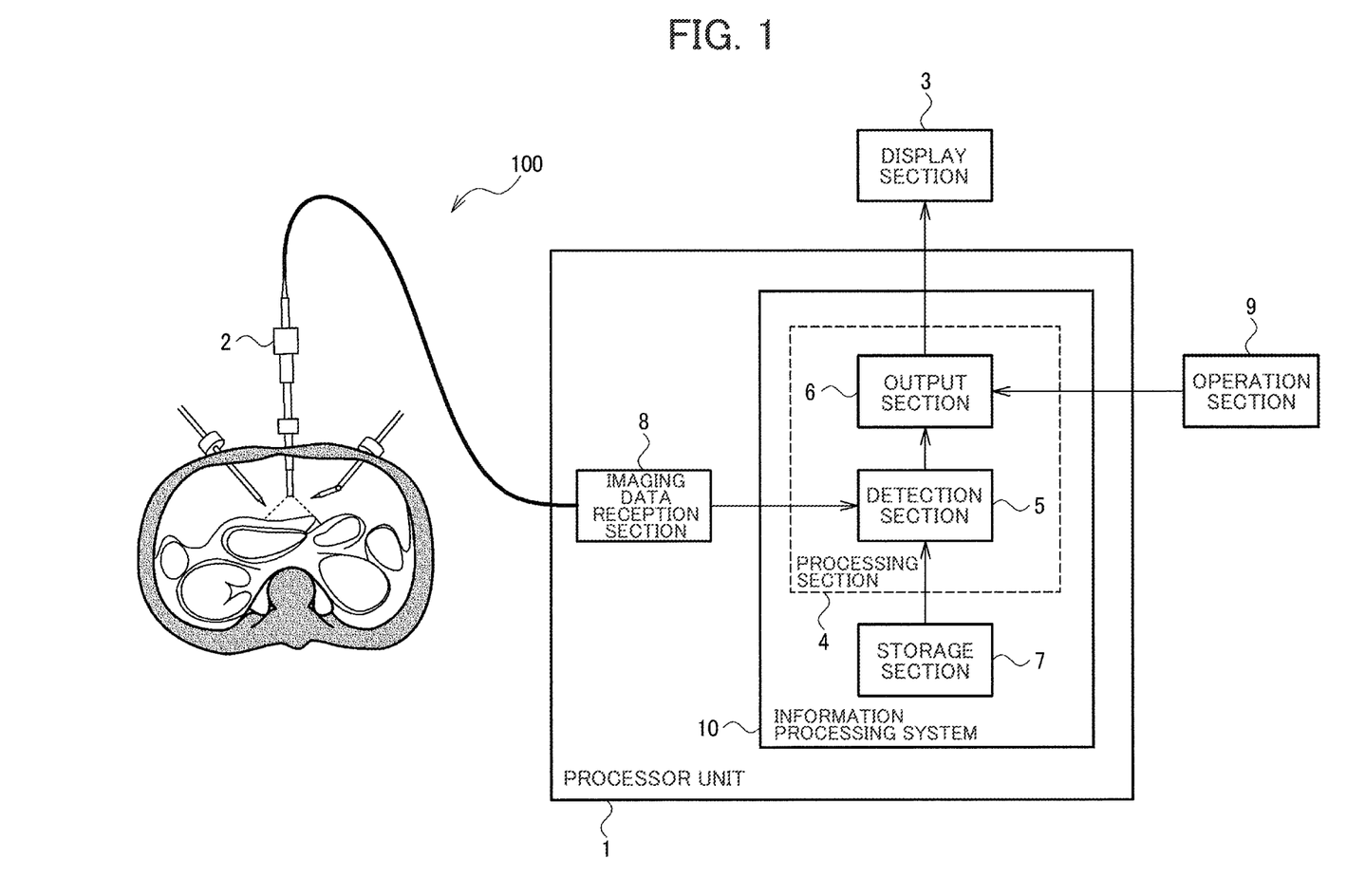
FIG. 1 illustrates a configuration example of an information processing system and an endoscope system including the information processing system, in accordance with the present embodiment.

FIG. 1 illustrates a configuration example of an information processing system 10 and an endoscope system 100 including the information processing system 10, in accordance with the present embodiment. The endoscope system 100 includes a processor unit 1, an endoscopic scope 2, and a display section 3. The endoscope system 100 may further include an operation section 9.

An imaging device is arranged at a distal end of the endoscopic scope 2, and the distal end is inserted into an abdominal cavity. The imaging device captures an image of the inside of the abdominal cavity, and imaging data of the image is transmitted from the endoscopic scope 2 to the processor unit 1.

The processor unit 1 is a device that executes various kinds of processing in the endoscope system 100. For example, the processor unit 1 performs control of the endoscope system 100, image processing, and the like. The processor unit 1 includes an imaging data reception section 8 that receives imaging data from the endoscopic scope 2, and the information processing system 10 that detects an object from the imaging data using a trained model.

The imaging data reception section 8 is, for example, a connector to which a cable of the endoscopic scope 2 is connected, an interface circuit that receives imaging data, or the like.

The information processing system 10 includes a storage section 7 that stores therein a trained model, and a processing section 4 that detects the object from an image based on the trained model stored in the storage section 7.

The storage section 7 is, for example, a storage device such as a semiconductor memory, a hard disk drive, or an optical disk drive. The trained model is preliminarily stored in the storage section 7. Alternatively, the trained model may be input to the information processing system 10 from an external device such as a server via a network, to be stored in the storage section 7.

The processing section 4 includes a detection section 5 and an output section 6. The detection section 5 detects the object from the image by inference using the trained model. The output section 6 causes the display section 3 to display information indicating the object superimposed on the image based on a result of the detection. Various kinds of hardware can be assumed as hardware to make an inference using the trained model. For example, the detection section 5 is a general-purpose processor such as a central processing unit (CPU). In this case, the trained model stored in the storage section 7 is composed of a program describing an inference algorithm and a parameter to be used for the inference algorithm. Alternatively, the detection section 5 may be a dedicated processor that implements the inference algorithm as hardware. In this case, the trained model stored in the storage section 7 is composed of a parameter to be used for the inference algorithm. A neural network may be applied to the inference algorithm. In this case, the parameter is a weight coefficient assigned between connected nodes in the neural network.

The display section 3 is a monitor to display the image output from the output section 6, and is, for example, a display device such as a liquid crystal display, an organic electroluminescence (EL) display, or the like.

The operation section 9 is a device for an operator to operate the endoscope system 100. The operation section 9 is, for example, a button, a dial, a foot switch, a touch panel, or the like. As described later, the output section 6 may change a mode of displaying the object based on input information from the operation section 9.

While the information processing system 10 is included in the processor unit 1, part or all of the information processing system 10 may be arranged outside the processor unit 1. For example, the storage section 7 and the detection section 5 may be implemented by an external processing device such as a personal computer (PC) or a server. In this case, the imaging data reception section 8 transmits imaging data to the external processing device via the network or the like. The external processing device transmits information indicating the detected object to the output section 6 via the network or the like. The output section 6 causes the display section 3 to display the received information superimposed on the image.

In surgery through an endoscope, there is a case where an operator is hard to identify an object whose position and shape are not clearly displayed in an image. For example, a state can be assumed in which in surgery through the endoscope, while procedures are taken using a predetermined landmark as a guide, the position and shape of the landmark are not clearly displayed in an image. At this time, there is a case where an inexperienced physician is hard to distinguish the unclear landmark. Note that the position and shape means a position and a shape.

The endoscope system 100 in accordance with the present embodiment detects the object whose position and shape are not clearly displayed in the image, and presents information indicating the detected object to the operator. Accordingly, the endoscope system 100 can present, for example, information indicating the position and shape of the unclear landmark on the image. In addition, the present embodiment provides the object whose position and shape are not clearly displayed in the image with an annotation when generating training data. For example, a physician who has rich experience in surgery through the endoscope or the like performs annotation. The present embodiment implements the detection and display of the object based on implicit knowledge of the experienced physician or the like by detecting the object using the trained model that is trained by machine learning using such training data.

Figure 2A:
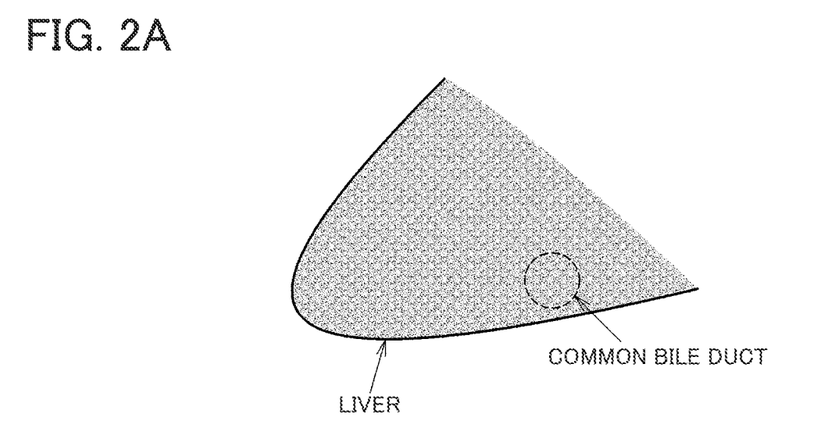
FIGS. 2A to 2C each illustrate an object whose position and shape are not clearly displayed in an image.
Figure 2B:
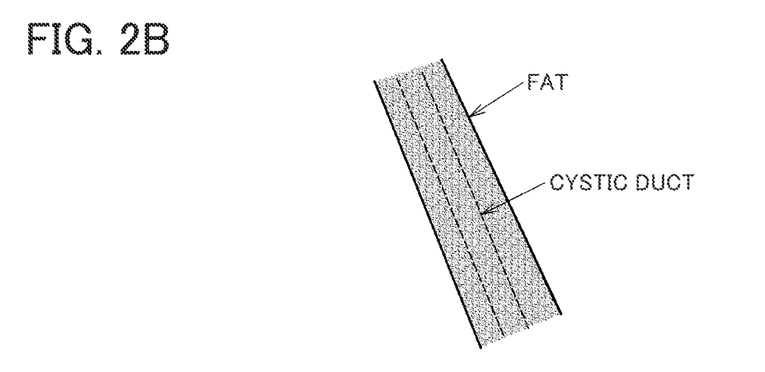
Figure 2C:
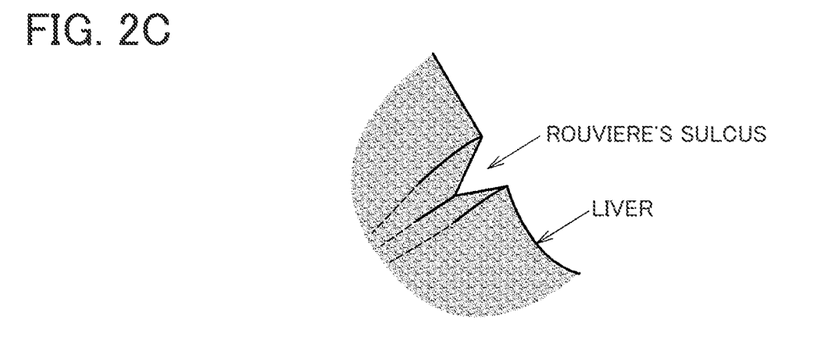

FIGS. 2A to 2C each illustrate an example of the object whose position and shape are not clearly displayed in the image. The common bile duct serves as the object in FIG. 2A, the cystic duct serves as the object in FIG. 2B, and the Rouviere's sulcus serves as the object in FIG. 2C. Note that FIGS. 2A to 2C are schematic diagrams, which do not illustrate accurate shapes of actual organs or tissues. The same applies to FIG. 4 and subsequent drawings.

FIGS. 2A and 2B each illustrate an example of a state where the object is covered with an organ or tissues. In this case, even when the object is present within the angle of view of a camera, the object itself is invisible in the image, or the position and shape of the object are not clear. Specifically, as illustrated in FIG. 2A, in an endoscopic image for cholecystectomy through laparoscopy, the common bile duct is covered with the liver, and the common bile duct itself is not displayed in the image. The common bile duct is a duct that connects a portion at which the common hepatic duct and the cystic duct join with each other, and the duodenum. As illustrated in FIG. 2B, the cystic duct is covered with fat, and the cystic duct itself is not displayed in the image. The cystic duct is a duct that connects the gallbladder and the common bile duct.

FIG. 2C illustrates an example of a state where the object is exposed visibly in the image but has an ambiguous boundary. As illustrated in FIG. 2C, in the endoscopic image for cholecystectomy through laparoscopy, the Rouviere's sulcus can be visually recognized, and the origin of the sulcus is relatively clear. However, since the sulcus gradually disappears toward its end, the boundary of the Rouviere's sulcus is ambiguous. The Rouviere's sulcus is a fissure that exists on a surface of the right lobe of the liver. In addition, another example of the object that can be visually recognized in the image but has an ambiguous boundary is the base of the S4, which is the inferior border inside the left lobe of the liver.

The common bile duct, the cystic duct, the Rouviere's sulcus, and the base of the S4 each serve as a landmark in cholecystectomy through laparoscopy. The landmark is a guide to be used at the time of taking procedures of a surgery. The present embodiment generates training data by performing annotation using these landmarks as the objects, and performs machine learning using the training data. The information processing system 10 of the endoscope system 100 detects the landmark using the trained model, thereby displaying on the image the position and shape of the landmark whose position and shape are not clearly displayed in the image.

As described above, the information processing system 10 in accordance with the present embodiment includes the storage section 7 that stores therein the trained model, and the processing section 4 that executes detection processing based on the trained model. The trained model is a training model trained to output the position and shape of the object in the training image based on the training data. The training data is data in which the training image is provided with an annotation indicating the position and shape of the object. The training image is an image captured with an angle of view including the object whose position and shape are not clearly displayed in the image. The processing section 4 executes detection processing on a detection image captured with an angle of view including the object to output detected information indicating the position and shape of the object. The processing section 4 causes the display section 3 to display the detected information superimposed on the detection image.

As a result, in some embodiments, in the detection processing using machine learning, the object whose position and shape are not clearly displayed in the image can be accurately detected, and the position and shape of the object can be displayed. In addition, by performing machine learning using the training data provided with an annotation indicating the position and shape of the object, the detection and display of the object based on implicit knowledge of the experienced physician or the like can be implemented.

In accordance with the present embodiment, the training image is a captured image of a state where the object is covered with another organ or other tissues, or a state where the object is exposed visibly but has an ambiguous boundary.

That is, since the object is covered with another organ or other tissues, the position and shape of the object are not clear in the image. Or the object is exposed visibly but has an ambiguous boundary in the image. In some embodiments, the position and shape of such an object is detected using the trained model, and thereby information indicating the position and shape of the object can be displayed in the image.

In accordance with the present embodiment, the object is a predetermined landmark at a predetermined surgery scene.

As illustrated in FIGS. 2A to 2C, there is a case where the position and shape of the landmark are not clear in the image. In some embodiments, the position and shape of such a landmark is detected using the trained model, and thereby information indicating the position and shape of the landmark can be displayed in the image.

Additionally, in accordance with the present embodiment, the training image is an image captured with an angle of view including at least one of the Rouviere's sulcus, the base of the S4, the common bile duct, or the cystic duct. The processing section 4 outputs detected information indicating the position and shape of at least one of the Rouviere's sulcus, the base of the S4, the common bile duct, or the cystic duct.

As a result, in some embodiments, information indicating the position(s) and shape(s) of one or more of the Rouviere's sulcus, the base of the S4, the common bile duct, and the cystic duct is detected and displayed. Taking the cystic duct as an example, since the cystic duct is covered with fat, the position and shape of the cystic duct are not clear in the image, as described with reference to FIG. 2B. In some embodiments, the position and shape of the cystic duct as described above is detected using the trained model, and thereby the information indicating the position and shape of the cystic duct covered with fat can be displayed in the image.

In addition, the trained model in the present embodiment may be stored in an information storage medium. The information storage medium is a computer-readable medium. The information storage medium may be any of various kinds of storage media, for example, an optical disk such as a digital versatile disk (DVD) or a compact disk (CD), a hard disk, and a semiconductor memory such as a nonvolatile memory or a read-only memory (ROM). The information processing system 10 executes various kinds of processing for the present embodiment, based on a program and data stored in the information storage medium. That is, the information storage medium stores therein the program causing a computer to function as the information processing system 10 of the present embodiment. The computer is a device including an input device, a processing section, a storage section, and an output section.

The trained model of the present embodiment can include a neural network. The neural network includes an input layer that takes input data, an intermediate layer that performs computation processing on the data input through the input layer, and an output layer that outputs data based on a result of the computation output from the intermediate layer. In the present embodiment, the data input to the input layer is the training image, and the data output from the output layer is the detected information indicating the position and shape of the object. Details of the input data and the output data will be described later. Note that the neural network may utilize various known artificial intelligence (AI) technologies. While use of the neural network requires development of software for execution of training or an inference algorithm, multiple software packages are currently available on the market or disclosed to the public for free, and the present embodiment can utilize such software packages. In addition, an algorithm for the machine learning in the neural network may be adopted from various known training algorithms, and a supervised training algorithm using backpropagation is preferably employed.

The processing executed by the information processing system 10 of the present embodiment may be implemented as an information processing method. That is, the information processing method is a method of executing the detection processing on the detection image captured with an angle of view including the object based on the above-mentioned trained model to output the detected information indicating the position and shape of the object, and causing the display section to display the detected information superimposed on the detection image.

2. Detailed Embodiment

Figure 3:
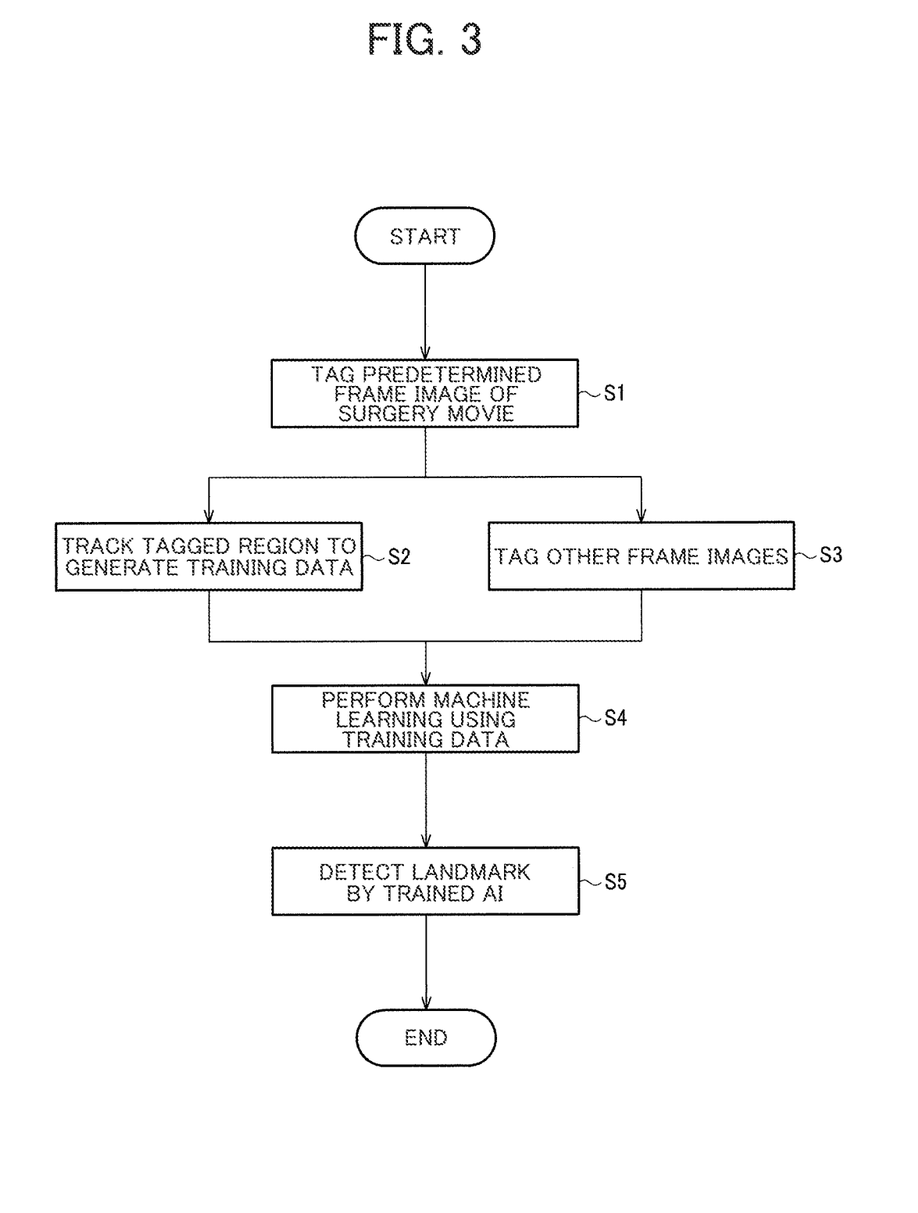
FIG. 3 is a flowchart illustrating a sequence of procedures from generation of training data to detection of an object in accordance with the present embodiment.

A detailed embodiment will be described below. FIG. 3 is a flowchart illustrating a sequence of procedures from generation of the training data to detection of the object in accordance with the present embodiment.

Steps S1 to S3 are steps for generating the training data. In step S1, an operator tags a predetermined frame image of a surgery movie. The operator is, for example, a physician or the like who is familiar with target surgery. As described later, the predetermined frame image is the first frame image after a scene change in the movie. Subsequently, in step S2, a training device tracks a tagged region to generate the training data. Alternatively, as indicated in step S3, the training data may be generated by the operator tagging each frame image. Each frame image of the surgery movie tagged in steps S1 to S3 serves as the training image. Note that tagging the image is referred to as annotation.

Step S4 is a training step. That is, the training device performs machine learning using the training data generated in steps S1 to S3. The trained model obtained by the machine learning is stored in the storage section 7 of the information processing system 10.

Step S5 is a step for making an inference by trained AI. That is, the processing section 4 of the information processing system 10 detects the object from the detection image based on the trained model stored in the storage section 7. The processing section 4 causes the display section 3 to display information indicating the detected object in the detection image.

Subsequently, a method of generating the training data will be described. The present embodiment generates the training data by providing the training image captured with an angle of view including the object whose position and shape are not clearly displayed in the image with an annotation indicating the position and shape of the object. As described above, the object can be used as the predetermined landmark in a surgery scene.

"The position and shape are not clearly displayed in the image" means a state where the position and shape of the object cannot be identified by a method of inferring a boundary based on a luminance or a contrast. For example, the object is any of the following objects in cholecystectomy through laparoscopy as described with reference to FIGS. 2A to 2C. A first example is an object that is covered with another organ, other tissues, or the like, and has an ambiguous boundary or an invisible boundary in the position and shape. The first example is, for example, the common bile duct and the cystic duct. A second example is an object that is exposed visibly in the image, but has an ambiguous boundary. The second example is, for example, the Rouviere's sulcus and the base of the S4.

With respect to the landmark whose position and shape are not clearly displayed in the image, the present embodiment identifies the position and shape in the image based on implicit knowledge of an operator and provides the identified position and shape as annotation data. The operator who performs annotation is a physician or the like who has extensive implicit knowledge about cholecystectomy through laparoscopy.

Figure 4:
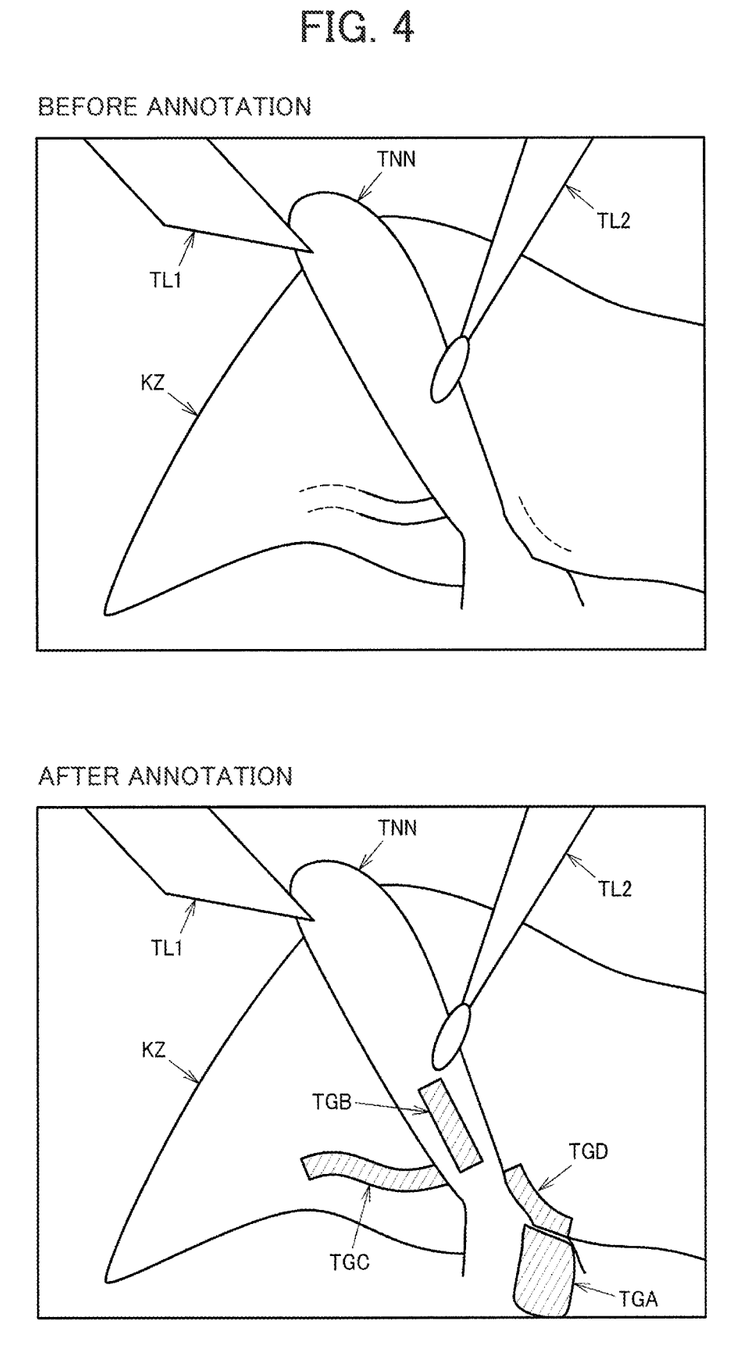
FIG. 4 illustrates an example of annotation.

FIG. 4 illustrates an example of annotation. A pre-annotation training image contains captured images of a liver KZ, a gallbladder TNN, and treatment tools TL1 and TL2. This training image includes, within its angle of view, the common bile duct, the cystic duct, the Rouviere's sulcus, and the base of the S4. In FIG. 4, a solid-line portion at the right lobe of the liver represents the origin of the Rouviere's sulcus (a relatively clear portion), and a dot-line portion represents gradual disappearance of the sulcus toward its end. Furthermore, a dot-line around the inferior border inside the left lobe of the liver represents a region of the base of the S4, which is the object that can be visually recognized in the image but has an ambiguous boundary.

The operator who performs annotation identifies and tags each of the common bile duct, the cystic duct, the Rouviere's sulcus, and the base of the S4 in the training image. A tag TGA indicating the common bile duct, a tag TGB indicating the cystic duct, a tag TGC indicating the Rouviere's sulcus, and a tag TGD indicating the base of the S4 are attached to a post-annotation training image. For example, the operator uses a pointing device such as a mouse or a touch panel to designate regions of the common bile duct and the like. The training device tags the regions designated by the operator in the training image.

Figure 5:
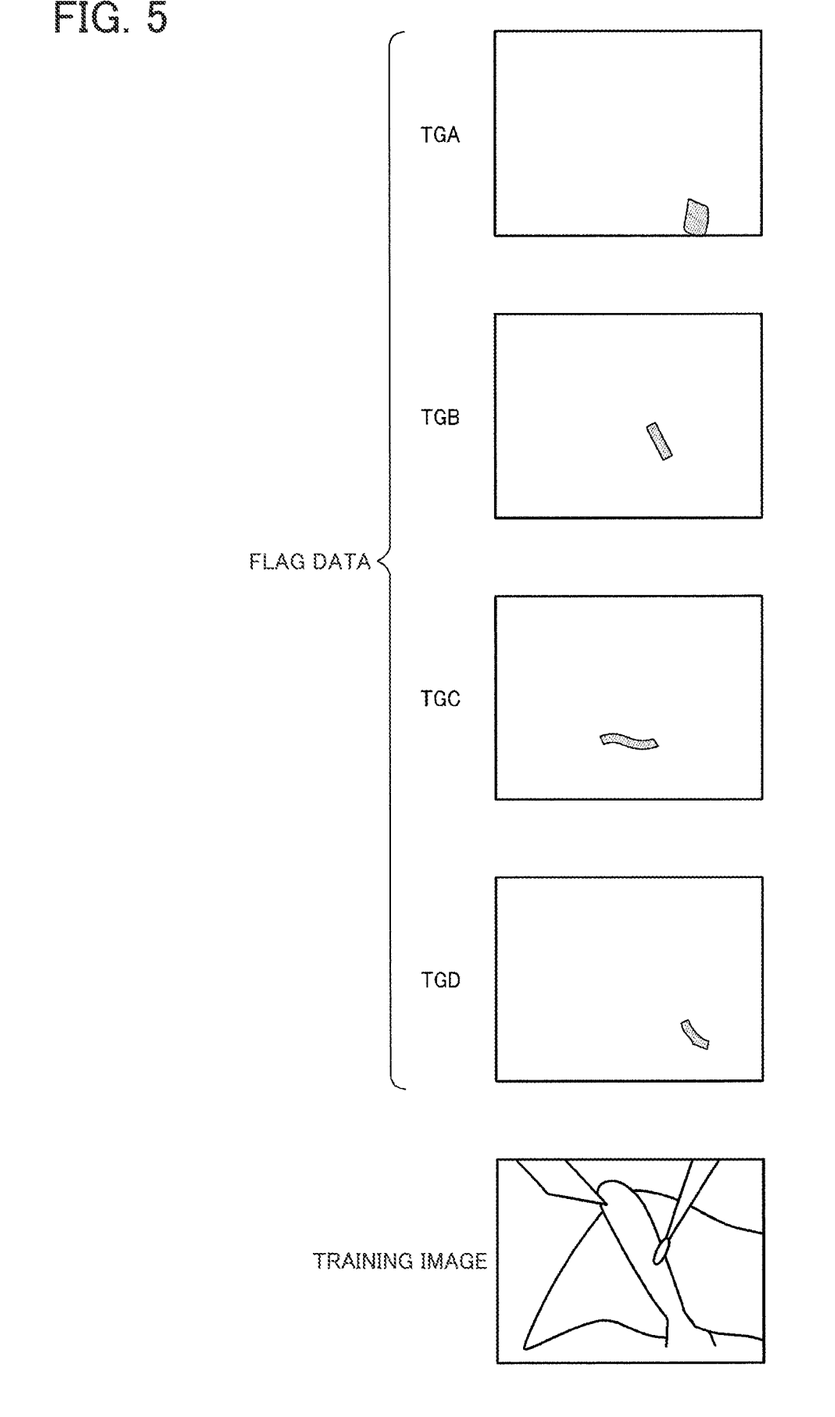
FIG. 5 illustrates an example of training data generated by the annotation.

FIG. 5 illustrates an example of training data generated by annotation. As illustrated in FIG. 5, a flag is attached to each of pixels in the tagged region. Map data in which the flag is attached to each of pixels is hereinafter referred to as flag data. The flag data is generated for each of the tags TGA to TGD. That is, the training data is composed of the training image and four-layer flag data generated by tagging the training image.

Figure 6:
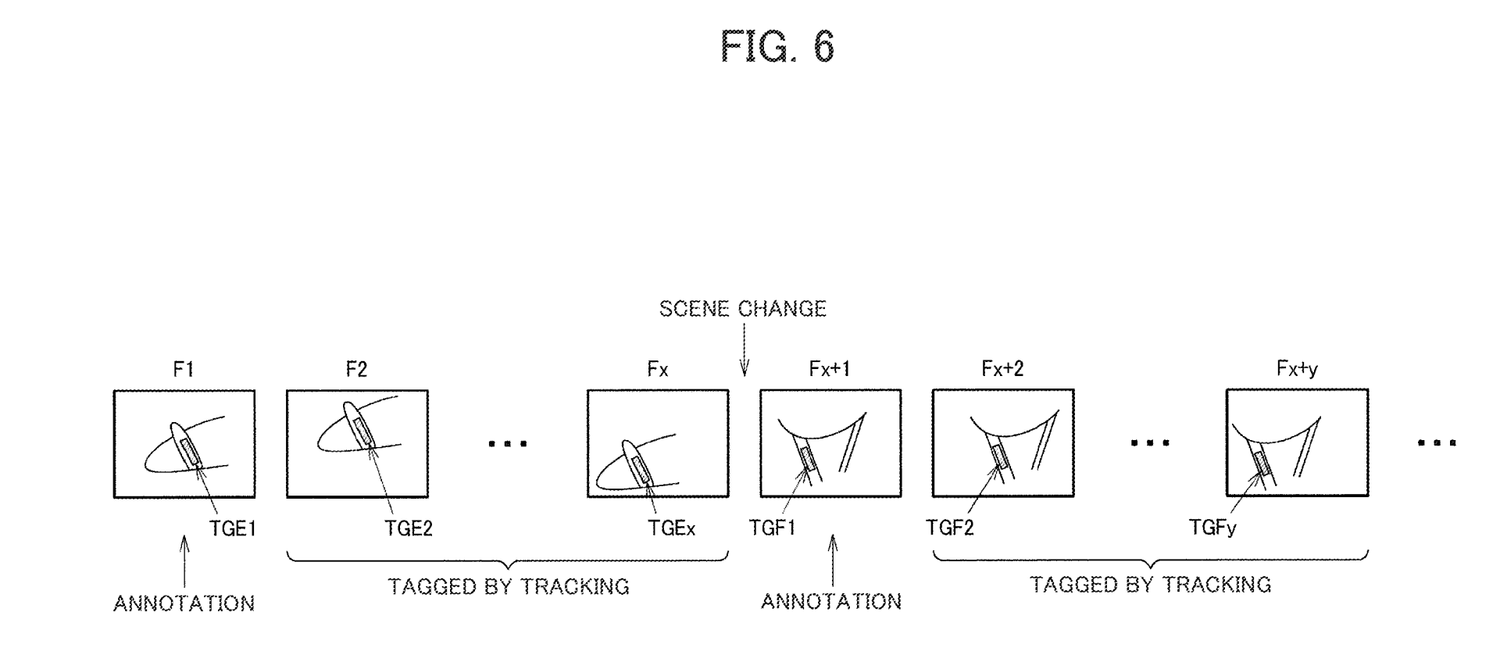
FIG. 6 illustrates automatic tagging by tracking.

FIG. 6 illustrates automatic tagging by tracking. FIG. 6 illustrates frame images of a movie captured by the endoscopic scope 2. These frame images each serve as the training image. Out of this movie, predetermined frame images F1 and Fx+1 are selected, where x is an integer of one or more. The operator may select the predetermined frame images F1 and Fx+1, or the training device may select the predetermined frame images F1 and Fx+1 by executing image processing to detect a scene or the like. The operator tags the selected predetermined frame images F1 and Fx+1.

Each of the predetermined frame images F1 and Fx+1 is, for example, a frame image when a surgery procedure is switched to another surgery procedure, a frame image when lightness or darkness changes in the movie, a frame image when a difference between frames is large, a frame image when an imaged object is switched to another imaged object, or the like.

Frame images subsequent to the tagged predetermined frame image are tagged by tracking. For example, tagging is performed by a method of extracting a contour from the tagged region, and tracking a point on the contour. Alternatively, motion of a subject may be detected using template matching, and tagging may be performed based on the detected motion.

Specifically, assume that the operator attaches a tag TGE1 to the frame image F1. If a scene changes between the frame images Fx and Fx+1, frame images F2 to Fx are targets of tagging by tracking. For example, a motion vector of the subject between F1 and F2 is detected by tracking. As described with reference to FIG. 5, the tag TGE1 is flag data. Translating this flag map in accordance with the detected motion vector generates flag data for F2, which serves as a tag TGE2 for F2. Similarly, tags TGE3 to TGEx are generated for F3 to Fx, respectively.

Similarly, assume that the operator attaches a tag TGF1 to the frame image Fx+1 after a scene change. Similarly to the above, tags TGF2 to TGFy are attached to frame images Fx+2 to Fx+y, respectively, by tracking, where y is an integer of one or more.

The embodiment described above attaches the flag to each pixel in the training image to perform annotation. The pixel to which the flag is attached is a pixel determined to be a pixel corresponding to the position and shape of the object in the training image.

As a result, in some embodiments, the operator identifies the object whose position and shape are not clearly displayed in the image from the training image and designates the identified region or the like, and can thereby tag pixels in the region. In addition, performing machine learning using the training data in which the flags are attached to pixels allows the trained model to output data in which the flags are attached to the corresponding pixels. The pixels to which the flags are attached correspond to the position and shape of the detected object. Hence, by superimposing the data output from the trained model on the detection image, the position and shape of the detected object can be displayed.

Additionally, the present embodiment attaches the flags to a region on which annotation has been manually performed in the predetermined frame images F1 and Fx+1 of the movie, in which each frame image is the training image. The present embodiment tracks the region on which annotation has been manually performed in frame images subsequent to the predetermined frame images F1 and Fx+1, and attaches the flags to the tracked region.

As a result, in some embodiments, the operator is only required to perform annotation on the predetermined frame images F1 and Fx+1 of the movie, which reduces the burden of the operator. In addition, training data is automatically generated by tracking, and thereby a plurality of pieces of training data in which the position, orientation, or like of the subject is changed in the image can be obtained. By performing machine learning using this training data, accuracy of detection of the object made by the trained model can be enhanced.

Subsequently, a training method will be described.

Figure 7:
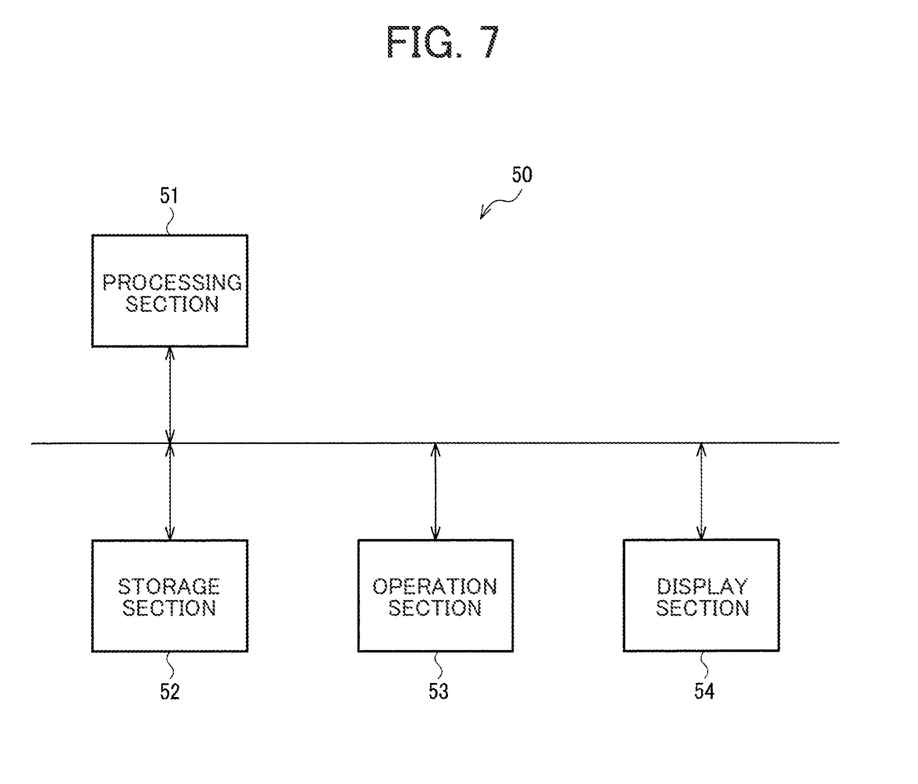
FIG. 7 illustrates a configuration example of a training device.

FIG. 7 illustrates a configuration example of a training device 50. The training device 50 includes a processing section 51, a storage section 52, an operation section 53, and a display section 54. For example, the training device 50 is an information processing device such as a PC. The processing section 51 is a processor such as a CPU. The processing section 51 performs machine learning on a training model to generate a trained model. The storage section 52 is a storage device such as a semiconductor memory or a hard disk drive. The operation section 53 is an operation input device of various types, such as a mouse, a touch panel, or a keyboard. The display section 54 is a display device such as a liquid crystal display.

Note that the information processing system 10 illustrated in FIG. 1 may also function as the training device. In this case, the processing section 4, the storage section 7, the operation section 9, and the display section 3 correspond, respectively, to the processing section 51, the storage section 52, the operation section 53, and the display section 54 in the training device 50.

Figure 8:
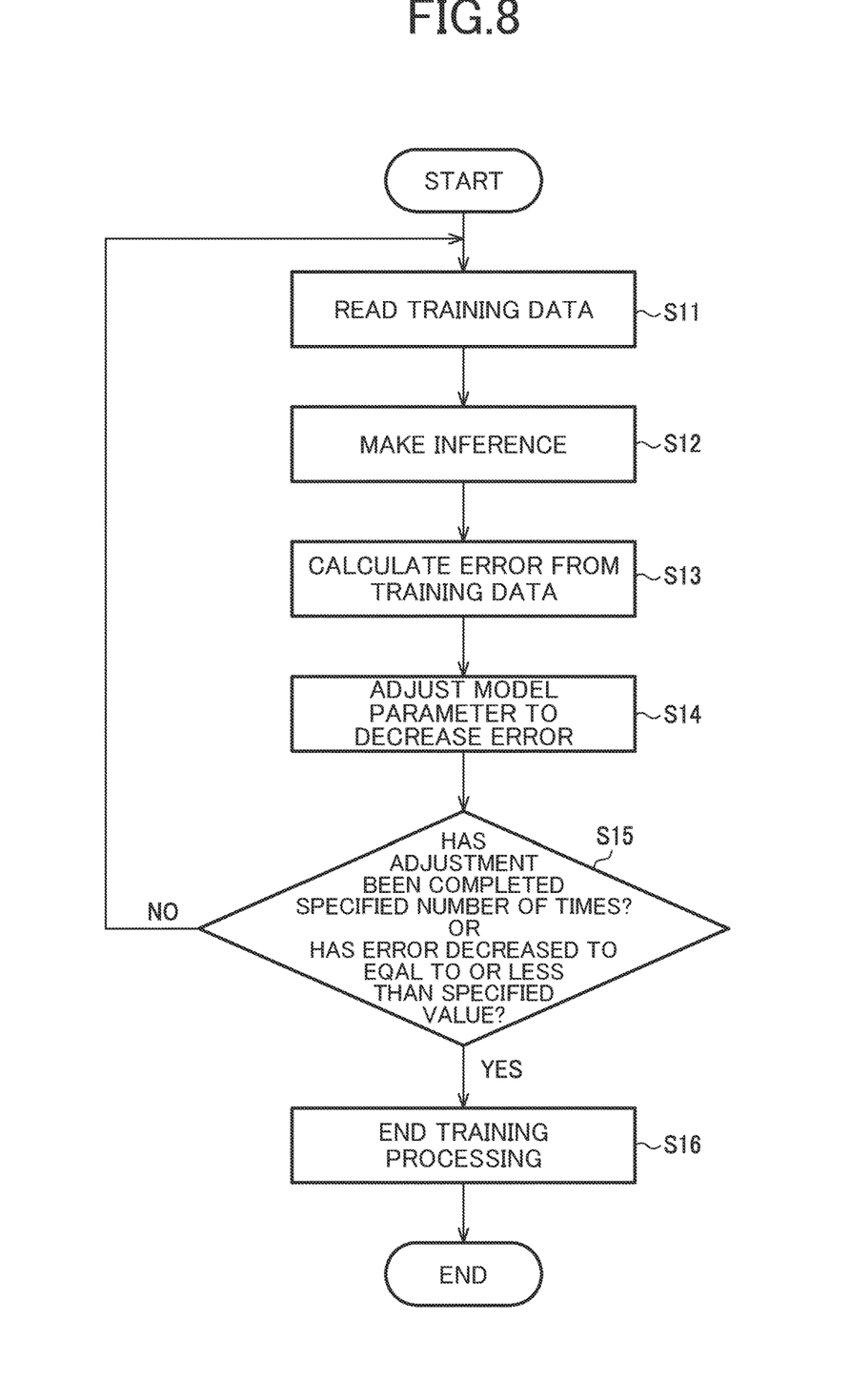
FIG. 8 is a flowchart illustrating a training procedure.

FIG. 8 is a flowchart illustrating a training procedure.

Training data is stored in the storage section 52. In step S11, the processing section 51 reads out the training data from the storage section 52. For example, for a single-time inference, the processing section 51 reads out one training image and corresponding flag data. Instead, multiple training images and corresponding flag data may be used for a single-time inference.

In step S12, the processing section 51 infers the position and shape of the object, and outputs a result of the inference. That is, the processing section 51 inputs the training image to a neural network. The processing section 51 executes inference processing using the neural network, and outputs flag data indicating the position and shape of the object.

In step S13, the processing section 51 compares the detected position and shape with a position and shape indicated by an annotation, and calculates an error based on a result of the comparison. That is, the processing section 51 calculates an error between the flag data output from the neural network and flag data of the training data.

In step S14, the processing section 51 adjusts a model parameter of the training model to decrease the error. That is, based on the error calculated in step S13, the processing section 51 adjusts a weight coefficient between nodes in the neural network, or the like.

In step S15, the processing section 51 determines whether the parameter adjustment has been completed a specified number of times. If the parameter adjustment has not been completed the specified number of times, the processing section 51 executes steps S11 to S15 again. If the parameter adjustment has been completed the specified number of times, the processing section 51 ends training processing as described in step S16. Alternatively, the processing section 51 determines whether the error calculated in step S13 has decreased to equal to or less than a specified value. If the error has not decreased to equal to or less than the specified value, the processing section 51 executes steps S11 to S15 again. If the error has decreased to equal to or less than the specified value, the processing section 51 ends the training processing as described in step S16.

In the present embodiment, the object whose position and shape are not clearly displayed in the image serves as a detection target for the AI. However, the training image is a medical image, and thus, besides the object, various subjects such as organs or tissues that cover the object or their surrounding organs or tissues appear in the training image. In machine learning, for example, the trained model is trained to learn a positional relationship between these subjects and the position and shape of the object provided with an annotation, or the like. This machine learning allows the trained model to estimate the position and shape of the object whose position and shape are not clearly displayed in the image from the detection image, i.e., the medical image.

Figure 9:
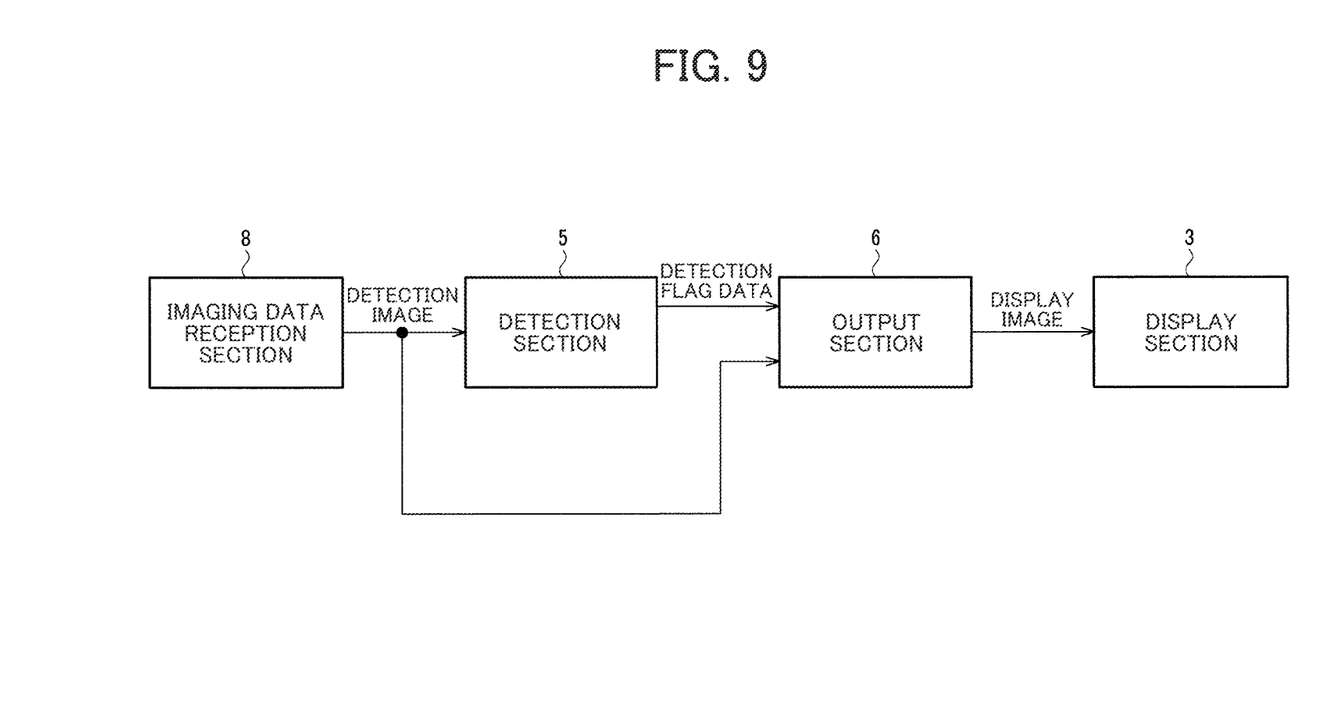
FIG. 9 is a block diagram illustrating a detection method and a display method.

Subsequently, a description will be given of a method in which the information processing system 10 detects the object and displays the object. FIG. 9 is a block diagram illustrating a detection method and a display method.

The detection section 5 inputs the detection image captured by the endoscopic scope 2 to the trained model. The detection section 5 executes detection processing using the trained model to infer the position and shape of the object in the detection image. That is, a detection result is output as detection flag data. The detection flag data is a flag map in which the flag is attached to each of pixels corresponding to the detected position and shape of the object. For example, similarly to the training data described with reference to FIG. 5, four-layer detection flag data corresponding to each object is output.

Figure 10:
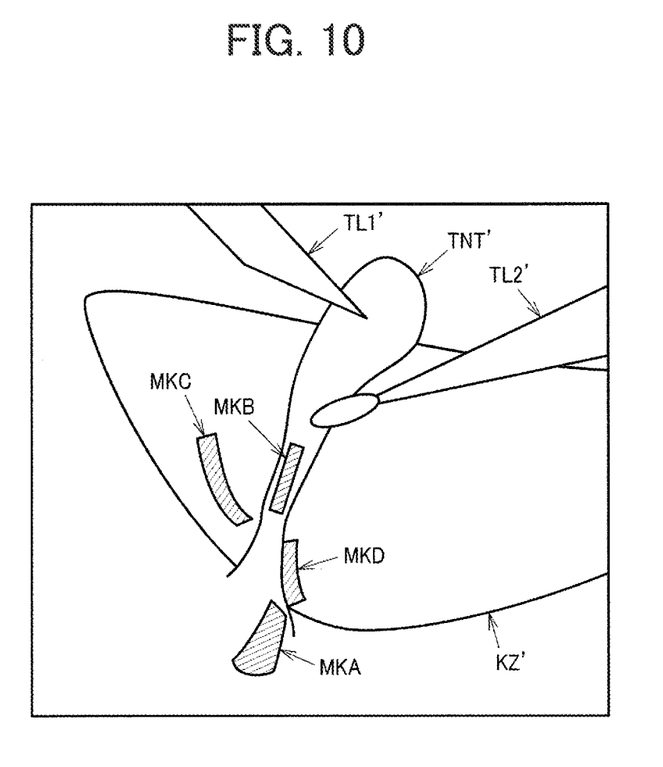
FIG. 10 illustrates an example of an image in which the position and shape of the detected object are displayed.

FIG. 10 illustrates an example of an image in which the detected position and shape of the object are displayed. KZ' indicates the liver, TNT' indicates the gallbladder, and TL1' and TL2' indicate treatment tools.

The output section 6 causes the display section 3 to display information indicating the detected position and shape of the object superimposed on the detection image. That is, the output section 6 executes image processing on pixels of the detection image corresponding to pixels to which the flags are attached in the flag data. The output section 6 outputs the detection image after the image processing to the display section 3. For example, the output section 6 provides the pixels of the detection image corresponding to the pixels to which the flags are attached with a predetermined color. Alternatively, the output section 6 superimposes the predetermined color with predetermined transmittance on the pixels of the detection image corresponding to the pixels to which the flags are attached. As illustrated in FIG. 10, the image processing described above highlights regions MKA to MKD corresponding to the respective positions and shapes of the objects. MKA is a region indicating the position and shape of the common bile duct. MKB is a region indicating the position and shape of the cystic duct. MKC is a region indicating the position and shape of the Rouviere's sulcus. MKD is a region indicating the position and shape of the base of the S4. As described above, the object can be detected in real time in a surgery movie captured during surgery, and the position information superimposed on the surgery movie can be displayed.

As described below, there are various kinds of methods of displaying the detected position and shape of the object. Note that the following methods may be combined as appropriate.

In a first method, the detection section 5 can detect the object exposed without being covered with another organ or other tissues together with the object covered with another organ or other tissues. When superimposing the detected information on the detection image, the output section 6 differentiates a mode of displaying the position and shape between the object covered with another organ or other tissues and the object exposed without being covered with another organ or other tissues.

That is, the output section 6 superimposes flag data indicating the object covered with another organ or other tissues on the detection image in a first display mode, and superimposes flag data indicating the object exposed without being covered with another organ or other tissues on the detection image in a second display mode. For example, the output section 6 superimposes a predetermined color with first transmittance on pixels to which the flags are attached, in the first display mode, and superimposes a predetermined color with second transmittance on pixels to which the flags are attached, in the second display mode. The first transmittance is higher than the second transmittance. Alternatively, the output section 6 superimposes a first predetermined color on pixels to which the flags are attached, in the first display mode, and superimposes a second predetermined color on pixels to which the flags are attached, in the second display mode. The first predetermined color and the second predetermined color are different colors. For example, in cholecystectomy through laparoscopy, the output section 6 provides pixels corresponding to the position and shape of the common bile duct and the position and shape of the cystic duct with the first predetermined color such as red. In addition, the output section 6 provides pixels corresponding to the position and shape of the Rouviere's sulcus and the position and shape of the base of the S4 with the second predetermined color that is different from the first predetermined color, such as yellow.

As a result, in some embodiments, the operator who uses the endoscope system 100 can easily recognize whether the displayed object is covered with another organ or other tissues, or exposed.

In a second method, when superimposing the detected information on the detection image, the output section 6 differentiates a mode of displaying the position and shape based on a predetermined degree of importance corresponding to the object.

That is, the output section 6 superimposes flag data indicating the position and shape of a first object having a first degree of importance on the detection image in the first display mode, and superimposes flag data indicating the position and shape of a second object having a second degree of importance on the detection image in the second display mode. For example, in a case where the first degree of importance is higher than the second degree of importance, the output section 6 causes the display section 3 to display the position and shape of the first object in a more highlighted manner than the position and shape of the second object. For example, in cholecystectomy through laparoscopy, assume that the common bile duct is set to have the first degree of importance, and the cystic duct, the Rouviere's sulcus, and the base of the S4 are set to have the second degree of importance. The output section 6 provides pixels corresponding to the position and shape of the common bile duct with the first predetermined color such as red. In addition, the output section 6 provides pixels corresponding to the position and shape of each of the cystic duct, the Rouviere's sulcus, and the base of the S4 with the second predetermined color that is a more subdued color than the first predetermined color, such as yellow. Alternatively, the output section 6 provides pixels corresponding to the position and shape of each of the cystic duct, the Rouviere's sulcus, and the base of the S4 with no color.

As a result, in some embodiments, in a case where a plurality of objects is displayed in the image, the object having a higher degree of importance can be presented to the operator in a more highlighted manner. For example, in a scene of dissection of the Calot's triangle in cholecystectomy through laparoscopy, when the operator grasps the gallbladder with a forceps to check the base of the S4, a degree of importance of the base of the S4 is increased and can be displayed in a more highlighted manner than other landmarks.

For example, the output section 6 determines a scene based on information input from the operation section 9 of the endoscope system 100. The output section 6 determines a degree of importance of the object corresponding to the determined scene. Alternatively, the output section 6 may use a predetermined degree of importance instead of determining a degree of importance in accordance with the scene.

In a third method, the output section 6 adds the name of the object that has been detected to the display when superimposing the detected information on the detection image.

That is, the output section 6 superimposes the flag data indicating the detected position and shape of the object on the detection image, and also adds the name of the object to the displayed position and shape. Furthermore, the output section 6 may add attribute information of the object to the display. The attribute information is, for example, information indicating whether the object is covered with another organ or other tissues or exposed, and the like. For example, in cholecystectomy through laparoscopy, the output section 6 provides a region corresponding to the position and shape of the common bile duct with a predetermined color, and causes the display section 3 to display "the common bile duct" as the name indicating the region provided with the predetermined color. The same applies to the cystic duct, the Rouviere's sulcus, and the base of the S4.

As a result, in some embodiments, the name or attribute information of the object whose position and shape are displayed can be presented to the operator. The operator can take procedures of surgery while checking which object each region in which the position and shape are indicated indicates.

In a fourth method, the output section 6 adds a degree of probability of a detection result of the object that has been detected to the display when superimposing the detected information on the detection image.

That is, the output section 6 superimposes the flag data indicating the detected position and shape of the object on the detection image, and also adds information indicating a degree of probability of the inference. For example, the detection section 5 outputs probability data indicating the degree of probability of the inference together with the flag data. For example, in a case where the detection flag indicating the cystic duct is attached to a pixel, data indicating a degree of probability is brought into correspondence with the pixel. The degree of probability mentioned herein is a degree of probability of inference that the pixel corresponds to the cystic duct. Data in which the data indicating the degree of probability is brought into correspondence with the pixel is probability data. For example, the output section 6 adds a value obtained by averaging the probability data with respect to the cystic duct within a screen to the position and shape of the cystic duct. The same applies to the common bile duct, the Rouviere's sulcus, and the base of the S4.

As a result, in some embodiments, the degree of probability of the inference with respect to the object whose position and shape are displayed can be presented to the operator. An operator such as a physician takes surgery procedures. By being presented with the degree of probability of the inference, the operator can take the surgery procedures in consideration of to what degree the detected position and shape of the object can be trusted.

In a fifth method, the output section 6 adds size information about the object that has been detected, when superimposing the detected information on the detection image.

That is, the output section 6 superimposes the flag data indicating the detected position and shape of the object on the detection image, and also adds the size information about the object to the displayed position and shape. As a method of measuring the size of the object, there is a method of referring to an object whose size is known such as a forceps whose image is captured during surgery. For example, the output section 6 seeks the length, area, or like of the detected position and shape in the image. The output section 6 seeks the length, area, or like of a forceps or the like whose image is captured during surgery in the image. Assume that the actual length or area of the forceps is a known value. The output section 6 compares the length, area, or like of the detected position and shape in the image and the length, area, or like of the forceps or the like whose image is captured during surgery in the image to acquire the size information about the object. In a case of a stereo endoscope, the output section 6 is capable of measuring the size of the object from parallax information.

As a result, in some embodiments, the size information about the object whose position and shape are displayed can be presented to the operator. Thus, the operator can take procedures of surgery in consideration of the detected size of the object. For example, in cholecystectomy through laparoscopy, the operator dissects the cystic duct while avoiding dissecting the common bile duct. At this time, length information about the common bile duct or the cystic duct serves as reference information in surgery, but there are variations in these lengths among individuals. The present embodiment presents the length information about the common bile duct or the cystic duct to the operator, thereby allowing the operator to take procedures of surgery in consideration of variations among individuals, and the like.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An information processing system comprising:
a storage device that stores therein a trained model; and
a processor that executes detection processing based on the trained model,
the trained model being trained to output the position and shape of the object in the training image based on training data, the training data being provided with an annotation indicating the position and shape of the object, the annotation being attached to the training image captured with an angle of view including an object whose position and shape are not clearly displayed in an image, and
the processor executing the detection processing on a detection image captured with an angle of view including the object, to output detected information indicating the position and shape of the object, and causing a display device to display the detected information superimposed on the detection image.

2. The information processing system as defined in claim 1,
the training image being an image obtained by capturing a state where the object is covered with another organ or other tissues or a state where the object is exposed visibly but has an ambiguous boundary.

3. The information processing system as defined in claim 1,
the annotation being provided by attaching a flag to each of pixels determined to be pixels corresponding to the position and shape of the object, in the training image.

4. The information processing system as defined in claim 3,
the flag being attached to a region manually provided with the annotation in a predetermined frame image of a movie in which each frame image is the training image, and
in frame images subsequent to the predetermined frame image, the region manually provided with the annotation being tracked, and the flag being attached to the tracked region.

5. The information processing system as defined in claim 1,
the object being a predetermined landmark in a predetermined surgery scene.

6. The information processing system as defined in claim 5,
the training image being an image captured with an angle of view including at least one of a Rouviere's sulcus, a base of an inferior border inside the left lobe of the liver, a common bile duct, or a cystic duct, and
the processor outputting the detected information indicating a position and shape of at least one of the Rouviere's sulcus, the base of an inferior border inside the left lobe of the liver, the common bile duct, or the cystic duct.

7. The information processing system as defined in claim 1,
the processor being capable of detecting the object that is covered with another organ or other tissues or the object that is exposed without being covered with another organ or other tissues, and
the processor, when superimposing the detected information on the detection image, differentiating a mode of displaying a position and shape between the object that is covered with another organ or other tissues and the object that is exposed without being covered with another organ or other tissues.

8. The information processing system as defined in claim 1,
the processor, when superimposing the detected information on the detection image, differentiating a mode of displaying a position and shape based on a predetermined degree of importance corresponding to the object.

9. The information processing system as defined in claim 1,
the processor, when superimposing the detected information on the detection image, adding a name of the object that has been detected to display.

10. The information processing system as defined in claim 1,
the processor, when superimposing the detected information on the detection image, adding a degree of probability of a detection result of the object that has been detected to display.

11. The information processing system as defined in claim 1,
the processor, when superimposing the detected information on the detection image, adding size information about the object that has been detected.

12. The information processing system as defined in claim 1,
the trained model being trained based on the training data including the training image and flag data in which a flag is attached to each of pixels determined to be pixels corresponding to the position and shape of the object in the training image, and
the processor executing the detection processing on the detection image to output, as the detected information, detection flag data in which a detection flag is attached to each of the pixels corresponding to the position and shape of the object.

13. The information processing system as defined in claim 12,
the processor executing processing of superimposing pixel data based on the detection flag on pixel data of the detection image to superimpose the detected information on the detection image.

14. An endoscope system, comprising:
a processor unit including the information processing system as defined in claim 1;
an endoscopic scope connected to the processor unit, and capturing the detection image and transmitting the detection image to the processor unit; and
the display device connected to the processor unit, and displaying the detection image on which the detected information indicating the position and shape of the object is superimposed.

15. A non-transitory information storage medium storing therein a trained model, the trained model being used for causing a computer to function to execute detection processing of accepting an input of a detection image to a neural network and detecting an object, and cause a display device to display detected information indicating a position and shape of the object in the detection image superimposed on the detection image, the neural network comprising:
an input layer taking input data:
an intermediate layer executing computation processing on the data input through the input layer; and
an output layer outputting data based on a computed result output from the intermediate layer, and
the trained model being trained to output the position and shape of the object in the training image based on training data, the training data being provided with an annotation indicating the position and shape of the object, the annotation being attached to the training image captured with an angle of view including an object whose position and shape are not clearly displayed in an image.

16. An information processing method of executing detection processing based on a trained model, the trained model being trained to output the position and shape of the object in the training image based on training data, the training data being provided with an annotation indicating the position and shape of the object, the annotation being attached to the training image captured with an angle of view including an object whose position and shape are not clearly displayed in an image,
the method comprising:
executing the detection processing based on the trained model on a detection image captured with an angle of view including the object, to output detected information indicating the position and shape of the object; and
causing a display device to display the detected information superimposed on the detection image.

* * * * *